US009814566B1

(12) United States Patent
Cree (10) Patent No.: US 9,814,566 B1
(45) Date of Patent: Nov. 14, 2017

(54) TISSUE EXPANDER INJECTION ASSEMBLIES

(71) Applicant: PMT Corporation, Chanhassen, MN (US)

(72) Inventor: Matthew W Cree, Chaska, MN (US)

(73) Assignee: PMT Corporation, Chanhassen, MN (US)

( * ) Notice: Subject to any disclaimer, the term of this patent is extended or adjusted under 35 U.S.C. 154(b) by 89 days.

(21) Appl. No.: 15/131,857

(22) Filed: Apr. 18, 2016

Related U.S. Application Data

(63) Continuation-in-part of application No. 13/959,315, filed on Aug. 5, 2013, now abandoned.

(60) Provisional application No. 61/742,691, filed on Aug. 15, 2012, provisional application No. 61/768,853, filed on Feb. 25, 2013.

(51) Int. Cl.
*A61F 2/12* (2006.01)

(52) U.S. Cl.
CPC .......... *A61F 2/12* (2013.01); *A61F 2210/009* (2013.01); *A61F 2210/0076* (2013.01); *A61F 2250/0003* (2013.01); *A61F 2250/0069* (2013.01); *A61F 2310/00011* (2013.01)

(58) Field of Classification Search
CPC ....................................................... A61F 2/12
USPC ....................................................... 623/7–8
See application file for complete search history.

(56) References Cited

U.S. PATENT DOCUMENTS

| | | | | |
|---|---|---|---|---|
| 6,743,254 B2* | 6/2004 | Guest | ........................ | A61F 2/12 623/8 |
| 2009/0118756 A1* | 5/2009 | Valencon | .............. | A61F 5/0036 606/192 |
| 2010/0049316 A1* | 2/2010 | Schuessler | ................ | A61F 2/12 623/8 |
| 2011/0152913 A1* | 6/2011 | Jones | ........................ | A61F 2/12 606/192 |
| 2011/0270391 A1* | 11/2011 | Chitre | ....................... | A61F 2/12 623/8 |
| 2011/0306827 A1* | 12/2011 | Chitre | ....................... | A61F 2/12 600/37 |
| 2014/0277440 A1* | 9/2014 | Martin | ...................... | A61F 2/12 623/8 |
| 2017/0189165 A1* | 7/2017 | Hristov | ..................... | A61F 2/12 |

* cited by examiner

*Primary Examiner* — Suzette J Gherbi
(74) *Attorney, Agent, or Firm* — Eggink & Eggink; Anthony G. Eggink; Katrina M. Eggink (57) ABSTRACT

An injection port assembly for a tissue expander and/or mammary prosthesis comprising a composite silicone matrix having embedded fiber layers. The composite matrix materials may cover or extend from the outside perimeter of the injection port assembly and provide self sealing polymeric materials if punctured by a needle. The tissue expander and injection port assemblies and structures may be formed of MR scannable materials. The injection port structures may have palpation lumps for locating the injection port structure subsequent implantation. The injection port structure may be remotely located from the tissue expander and connected thereto via tubing.

20 Claims, 7 Drawing Sheets

TISSUE EXPANDER INJECTION ASSEMBLIES

This Application is a Continuation in Part of application Ser. No. 13/959,315 filed on Aug. 5, 2013 and claims the benefit of Provisional Patent Application Ser. No. 61/742,691 filed on Aug. 15, 2012 and Ser. No. 61/768,853 filed on Feb. 25, 2013.

BACKGROUND OF THE INVENTION

The present invention relates generally to injection assemblies for soft tissue expander devices. Particularly, the invention relates to improvements to injection port assemblies for filling soft tissue expanding devices such as tissue expanders and mammary prosthesis. The injection assemblies utilize composite silicone materials having fiber mesh layers embedded therein. The composite materials of the invention may cover and/or extend from an injection port structure and which are constructed to self seal when punctured by a hypodermic filling needle, for example. The invention further relates to injection port structures constructed of MR safe and/or MR conditional materials to provide tissue expander structures safe for scanning by a Magnetic Resonance Imager (MRI), for example.

The present invention provides improved injection port and injection area assemblies for soft tissue expanders. The injection ports of the invention improve upon prior art injection port structures to thereby assist the user, e.g., medical technician, practitioner or physician, in performing various medical procedures related to tissue expanders and/or mammary prosthesis. For example, U.S. Pat. No. 6,743,254 ('254 Patent) describes a tissue expander with protection against accidental puncture, however, the '254 Patent discloses a silicone matrix which is swelled by exposure to dimethylpolysiloxane, adhered into a tissue expander and a hole is punched through this material to locate the injection port. The '254 Patent discloses a two piece design, which requires both a tolerance space in between the injection port and silicone matrix, as well as adhesion of the injection port on the external surface of the soft tissue expansion device. The '254 Patent two piece design could potentially allow a needle puncture in between the silicone matrix and the injection port assembly and requires the injection port assembly to extend past the soft tissue expansion device silicone shell in order to seal the device on the external surface during final device assembly.

Additionally, patent application publications No. US20110270391 and No. US20090118756 teach the use of silicone gel or other viscous fluid under compression to facilitate the closing of injection needle paths to effectively self-seal soft tissue expansion devices. The utilizing of silicone gel or other viscous fluid complicates the device assembly and increases the costs associated with manufacturing.

Further, prior art U.S. Pat. No. 4,685,447 teaches the use of a metal plate and x-ray procedure to locate an injection port and U.S. Pat. No. 6,588,432 discloses a tissue expander system that utilizes a magnet for locating an injection port located under the skin. Although the injection port structures of these patents have been proven useful, occasionally medical personnel will miss the intended injection location near the center of the injection port. The present invention increases the probability of a successful tissue expander filling procedure with a reduced probability of leakage caused by needles missing the injection port and puncturing the shell of the tissue expander and/or mammary prosthesis.

The present invention resolves potential issues relating to prior art structures, that utilize two piece designs, by integrating a silicone composite of Dacron® fibers, i.e., polyester fibers, and silicone rubber into a unitary injection port structure. The one piece unitary structure of the invention eliminates the possibility of a needle puncture in-between the port and protective silicone matrix. The present invention also protects the tissue expanding device from accidental needle puncture by a resealing characteristic which is achieved without the use of a swelling agent in the manufacturing process, such as described in the prior art '254 Patent. The unitary composite self sealing ring of the invention overcomes the shortcomings and limitations of the prior art.

The present invention reduces manufacturing costs and time required in patent application publications No. US20110270391 and No. US20090118756, as the present unitary self-sealing injection port does not need to encapsulate a low durometer silicone gel or viscous fluid layer within the self-sealing silicone composite to self-seal leak causing needle paths after an injection. The present invention utilizes two or more layers of polyester mesh, positioned at the correct depth and orientation, to effectively self-seal a composite silicone matrix material having a single durometer reading adhered within a soft tissue expansion device. The elimination of a silicone gel or viscous fluid layer within the silicone composite material is a desired improvement by reducing material costs and time associated with manufacturing.

The present invention further improves upon the limitation of prior art devices to thereby assist the user (e.g. medical technician, practitioner or physician) in performing various medical procedures related to the device. The invention resolves potential issues for the patient encountered by prior art injection port structures having ferrous or metallic parts, such as stainless steel or magnets, and which restrict the patient from having imaging performed with an MRI, which subjects the device to a magnetic resonance field. The tissue expander injection port configuration of the invention improves the device by replacing the components affected by the MR field created by a Magnetic Resonance Imager with MR scannable, i.e., MR safe and/or MR conditionally safe materials.

The terminology defined in ASTM F2503 and recognized by the FDA are as follows: MR safe: An item that poses no known hazards in all MR imaging environments. With this terminology, MR safe items are non-conducting, nonmetallic, and nonmagnetic items. MR conditional: An item that has been demonstrated to pose no known hazards in a specified MR environment with specified conditions of use. The materials utilized in this invention relate to implantable soft tissue expanders capable of being subjected to the magnetic fields resulting from MRI equipment used in medical environments. The biocompatible MR safe and/or MR conditional materials may include PEEK, HDPE, titanium and like materials. MR safe and/or MR conditional materials are referred herein collectively as MR scannable materials unless specifically referring to either as MR safe or MR conditional material.

A tissue expander and other inflatable and inplantable devices are typically injected using a hypodermic needle or similar device by filling the injection port which is in communication with the tissue expander. For example, Applicant assignee's prior art, U.S. Pat. No. 4,685,447 (Iversea et al.) teaches the use of a metal plate and an x-ray procedure to locate an injection port, and U.S. Pat. No. 6,588,432 (Rehder et al.) describes a tissue expander system that utilizes a magnet for locating the injection port under the skin. While these patents have proven to be useful for locating an injection port, they are not MR scannable devices. Subsequent implantation of an above referenced prior art device, the patient cannot and should not be exposed to the magnetic forces used by an MRI due to the use of metallic and magnetic parts within the injection port structures. The present invention allows a tissue expander or similar inflatable device to be injected with a saline or similar fluid, using a hypodermic needle or similar device, without restricting the patient's access to high strength magnetic fields, such as being scanned by an MRI after the device has been implanted.

SUMMARY OF THE INVENTION

An injection assembly for a soft tissue expansion device. The injection assembly comprises a resealing matrix material which may be incorporated into the tissue expander structure or in communication via tubing with the tissue expander. The injection assembly may include a port structure having an integrated resealing ring for a soft tissue expanding device such as a tissue expander or mammary prosthesis. The resealing matrix material may comprise a vulcanized silicone and a fiber mesh composite material which may be utilized to surround the outside perimeter of an injection port as a one piece design to protect the tissue expander from accidental puncture by a needle outside of the injection port and through the integrated silicone composite. The latter one piece or unitary structure comprising an injection port having a resealing ring structure around the injection area wherein the resealing ring comprises embedded or integrated layers of a fiber mesh material as further described with respect to FIGS. 1-5 and FIG. 8. The resealing composite structure provides a medical technician, practitioner or physician with a protective resealing ring integrated into the device injection port, thereby reducing the probability of leakage caused by an accidental needle puncture outside the injection port during tissue expander filling procedures.

The resealing assembly or port structure may be comprised of a vulcanized silicone composite material having embedded fiber mesh layers, oriented in a predetermined direction, to prevent the elongation of the composite material and to thereby provide resealing characteristics when punctured by a hypodermic needle. The fiber layers of the Dacron® or polyester material within the silicone structure provide for the self sealing characteristics of the resealing injection area or ring structure. The mesh fibers of the composite layers are preferably oriented in perpendicular or other predetermined directions to thereby maintain the mechanical structural integrity of the silicone layers of the composite material.

Injection assemblies and ports for tissue expanders of the invention may also be constructed of MR scannable materials. Tissue expanders are typically manufactured from silicone, which is known to be an MR safe material. Thus, using MR safe or MR conditional materials to create a functioning injection port results in the completed device being MR scannable and allows the device to be safely scanned by a Magnetic Resonance Imager (MRI).

The present invention may further utilize MR scannable materials in the injection port structure. Since the injection port will not have a magnet and may be radiolucent, locating the injection port may be accomplished by providing a distinct lump or like feature on the tissue expander detectable via a doctor's palpitation. Additionally, a physician may utilize a mobile ultrasound or like device to locate the tissue expander and injection port. The MR scannable injection port may be of various sizes. The MR scannable injection port may also be integrated inside of the tissue expander and/or be remotely located and connected to the expansion device via tubing.

The invention may also utilize MR scannable materials for associated cooperating items that may be required for use in conjunction with the tissue expander. Accessory items may include various sizes of MR scannable tubing connectors and various sizes of MR scannable remotely located injection areas or port structures.

An advantage of the present invention is to integrate a self sealing silicone composite matrix material into an injection area or port assembly as a one piece structure. The composite resealing matrix may be formed into a ring structure that is integrated into various tissue expander structures and into injection port structures, including injection ports that incorporate a magnet for non-invasive port location using a hand held magnetic port locator.

The silicone composite material of the invention is constructed to reseal, without the use of swelling agents, when punctured by a 21 gauge or smaller hypodermic needle or infusion needle, for example, protecting the tissue expander from accidental needle puncture outside of the injector port.

These and other advantages of this invention will become clear from the following description by reference to the drawings.

DESCRIPTION OF THE PREFERRED EMBODIMENTS

Figure 1:
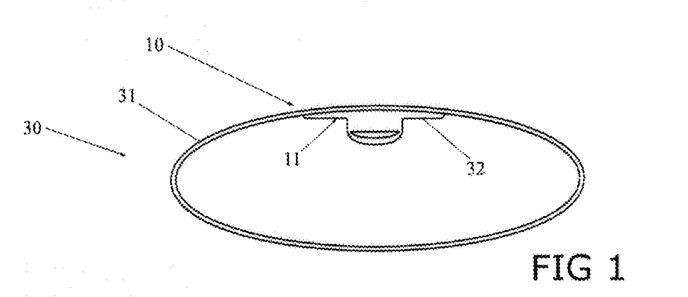
FIG. 1 is a lateral sectional view showing the injection port assembly with a resealing ring of the invention and showing the injection port incorporated into a tissue expander.
Figure 7:
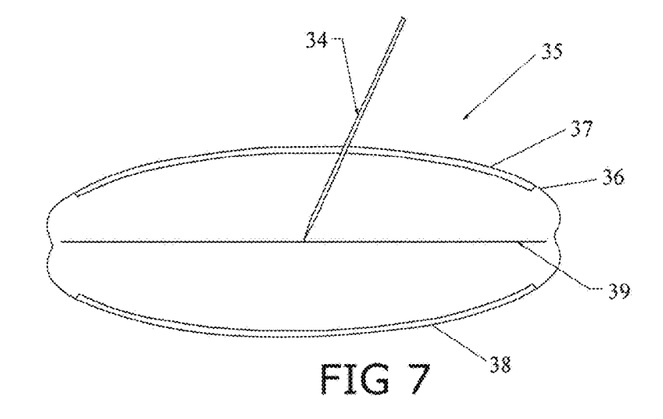
FIG. 7 is a lateral plan view showing a tissue expander having a resealing silicone matrix forming an injection area.

The present invention provides a use with an improved injection area for a soft tissue expander as well as the reduced probability of leakage and/or damage of the tissue expander shell caused by an accidental needle puncture outside of the injection port but within the integrated silicone composite, so that multiple filling procedures can be performed. The injection port improvement reduces the probability for leakage caused by needle injections outside of the injection port but through the silicone composite material, as shown in FIG. 1. The injection port 10 shown in the drawings and described herein is exemplary of an injection port assembly for an implantable device, such as a soft tissue expanding device or mammary prosthesis. The resealing ring of the invention may be utilized with other injection port structures or incorporated independently into an implantable expanding device to provide a fluid injection area, as shown in FIG. 7, for example.

Figures 2, 2A, 3:
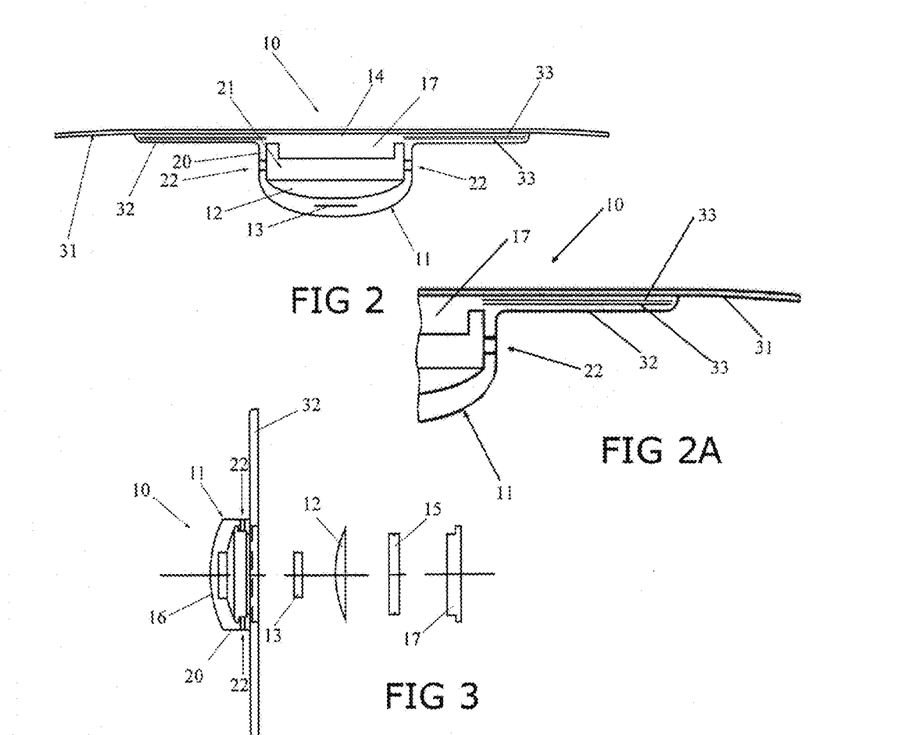
FIG. 2 is a cross-sectional view showing the injection port assembly of FIG. 1.
FIG. 2A is an enlarged view showing the injection port assembly of FIG. 2.
FIG. 3 is an assembly view of the injection port with resealing ring showing various components of the port.

FIG. 2 shows a one piece injection port structure 10 with an integrated silicone composite material located beneath the tissue expander shell material 31, the latter being a polymeric shell formed of silicone for example. As further discussed with respect to FIG. 8, predetermined composite materials, fiber mesh orientation and material thicknesses are required to create the resealing characteristic of the silicone composite, so that the tissue expander can be protected from accidental punctures. The injection port assembly 10 is shown having a formed body 11 that is generally cylindrical in shape, and having the resealing ring structure 32 with embedded fiber ring layer 33 extending from the outside perimeter of the top portion 14 of the injection port. The resealing ring structure 32 is also referred to as a resealing silicone matrix composite structure as further discussed below with respect to FIG. 8. The injection port 10 is shown comprised of a port top portion 14, an outside lateral wall member 20 and needle guard member 12 which define and form an injection port cavity 21. A magnetic element 13 may be incorporated into the port structure for port location purposes. A hypodermic needle or similar device may be inserted through the top portion 14 and into the injection port cavity 21 to inject a saline solution or other biocompatible fluid for expansion purposes. Fluid flows from the cavity 21 to the tissue expander system 30 via a means of fluid communication i.e., ports 22.

FIG. 2A is an enlarged view of a portion of the injection port assembly 10 showing two fiber mesh layers 33 embedded within the resealing ring structure 32, as further discussed below with respect to FIG. 8.

Figure 3A:
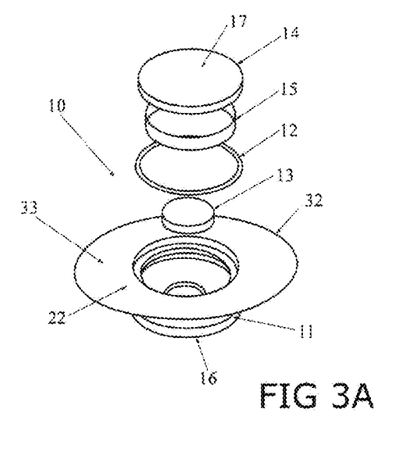
FIG. 3A is an assembly view in perspective of the port assembly of FIG. 3.
Figure 3B:
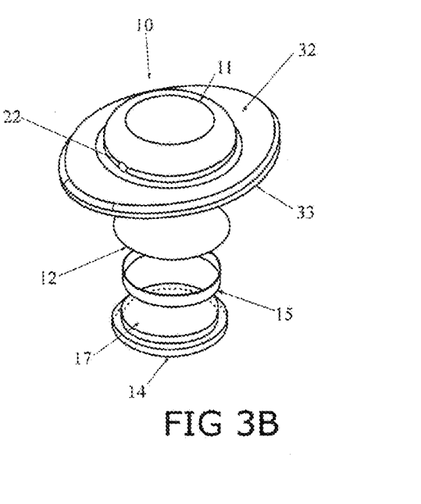
FIG. 3B is an assembly view in perspective of an alternative embodiment of the port assembly of FIG. 3.
Figure 4:
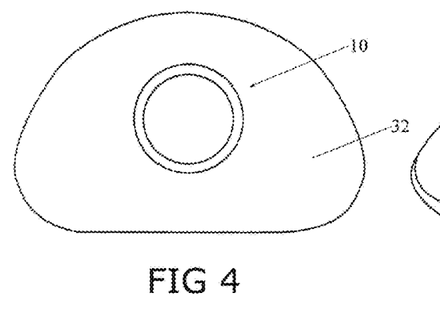
FIG. 4 is a perspective top view showing the injection port with an integrated resealing ring.
Figure 5:
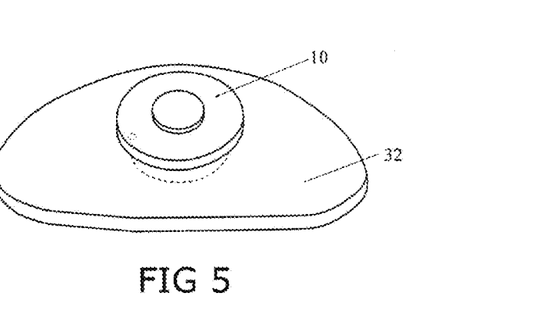
FIG. 5 is a perspective bottom view of the invention of FIG. 4.

FIG. 3 shows the injection port assembly 10 having a formed body 11 that is generally cylindrical in shape and which is comprised of an injection port top portion 14, an outside lateral wall 20 and a port bottom portion 16. The top portion 14 of the injection port body 11 together with ring member 15 and needle guard member 12 define and form injection port cavity 21. FIGS. 3A and 3B show the various components of injection port assembly 10 in an unassembled state. FIGS. 4 and 5 show the injection port assembly 10 in the assembled state. FIG. 3A shows the use of magnetic source 13 whereas the port structure of FIG. 3B does not. Both embodiments utilize top portion 14 having thickened portion 17 which is retained by ring member 15 which provides compressive forces for resealing purposes. FIGS. 3-3B all show the utilization of the resealing silicone matrix composite ring structure 32 extending from and being unitary with the injection port body 11.

Figure 6:
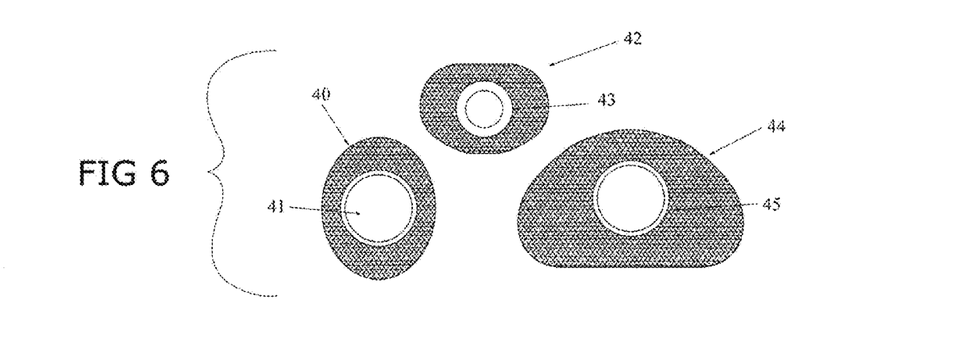
FIG. 6 shows various shapes of the resealing ring of the invention.

Referring to FIGS. 4 and 5, the front and back portions of the one piece injection port structure 10, with a protective resealing ring structure 32, are shown in an assembled state. The perimeter shape shown is of a semi-oval configuration which may be expanded. As shown in FIG. 6, various reseal ring shapes may be utilized and may be specifically designed for other tissue expander structures. For example, reseal ring assembly 40 is shown having an oval shape and injection port 41, reseal ring assembly 42 is shown having an elongated rounded shape and injection port 43 and reseal ring assembly 44 is shown having a semi-oval shape and injection port 45. It is within the purview of the invention to provide reseal ring shapes which may provide any predetermined geometric shapes for the soft tissue expanders into which they are incorporated.

FIG. 7 shows a soft tissue expander device 35 without a traditional injection port structure, and whereby injections can be made thru one side of the opposing resealing silicone matrix areas 37 and 38 which are vulcanized to the interior walls of shell 36 of the tissue expander 35. A needle stop plate 39 is provided in the interior of the expander device shell 36. The silicone matrix 37, 38 includes at least one, and preferably two, polyester fiber layers to provide mechanical strength and stability to the silicone composite structure. Additionally, the fiber layers are oriented oppositely, i.e., perpendicularly, to provide the mechanical strength in all directions. The resealing silicone matrix structure here shown may be particularly useful for relatively smaller soft tissue expanders.

Figure 8:
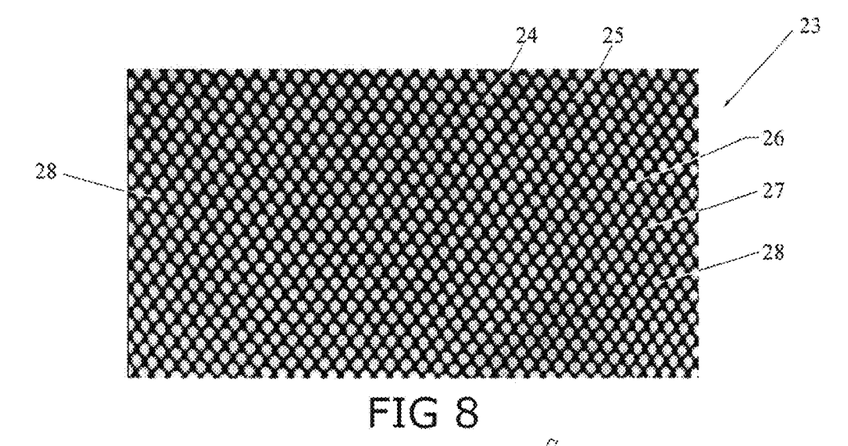
FIG. 8 is a top view of a portion of the polyester mesh reinforced silicone sheeting used to form the resealing structure of the invention.

FIG. 8 shows the polyester mesh reinforced silicone sheeting 23 utilized in the resealing silicone matrix composite of the invention. The sheeting material is a polyester mesh embedded in silicone 28 and two such sheets oppositely directed, i.e. mesh at 90 degrees with respect to each other, is preferably utilized to provide a silicone/polyester sheeting/silicone/polyester sheeting/silicone structure which is then vulcanized to the interior of the polymeric shell, i.e., the silicone sheet (shell) of the soft tissue expander device. Thus, oppositely directed mesh sheets 23, each having a polyester mesh embedded in silicone are utilized with additional layers of silicone to form the various resealing silicone matrix composite structures of the invention. For example, in FIGS. 1-5, a resealing silicone matrix composite ring shaped structure 32 is shown having the polyester mesh sheeting 33 therein. The ring shaped resealing silicone matrix composite 32 is shown incorporated with port body 11 to form a unitary injector assembly structure, which is vulcanized onto the inside of the tissue expander shell 31. It is within the purview of the invention to utilize other fiber mesh materials 24-27 to provide the lightweight mechanical strength to the silicone material to provide self sealing characteristics.

The oppositely oriented mesh layers within the resealing silicone matrix composite material provides mechanical stabilization properties to the materials so as to provide the resealing characteristics of the material. The silicone matrix composite material may have a durometer Shore A range of 20 to 50, and preferably an approximately 30 Shore A reading.

Figure 9:
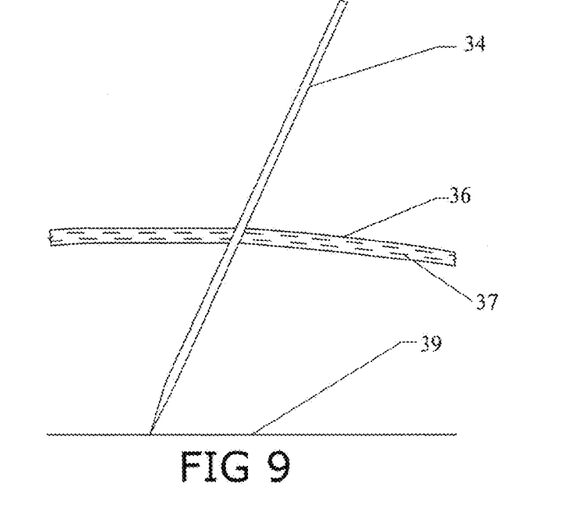
FIG. 9 is an enlarged view showing the polyester fibers of the resealing injection structures of the invention.

FIG. 9 is an enlarged view showing the polyester fiber mesh of FIG. 8 incorporated into the resealing injection area of the tissue expander of FIG. 7. Two polyester fiber mesh layers 37, oppositely oriented, are shown utilized to provide the lightweight mechanical stabilization of the silicone matrix so that the silicone composition reseals as the hypodermic filling needle 34 is removed.

Figure 10:
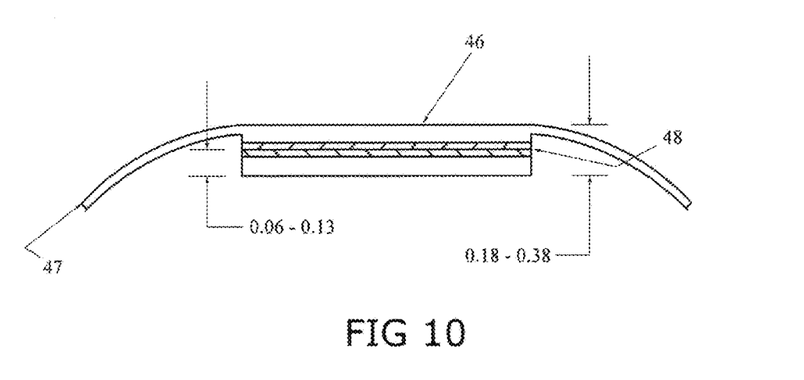
FIG. 10 is an enlarged partial, sectional view showing a resealing silicone composite injection area for a tissue expander.

FIG. 10 is an enlarged sectional view showing a resealing silicone composite structure 46 formed on the inside of a soft tissue expander shell wall 47 to provide an injection area. The resealing silicone composite structure 46 is shown to have two reinforcing mesh layers 48 which preferably are polyester fibers mesh layers having opposite directional fiber orientations when combined within the silicone composite matrix. The overall thickness of the injection area is shown to range from approximately 0.18 to 0.38 inches. Each reinforcing mesh layer 48 utilized has a thickness of approximately 0.02 inches. As shown, both the areas above and below the mesh layers are greater than and preferably at least twice the thickness of the combined polyester fiber layers. The latter structure providing a mechanically stable injection area structure whereby the reinforcing mesh reseals the silicone layers subsequent a filling procedure.

Figure 11:
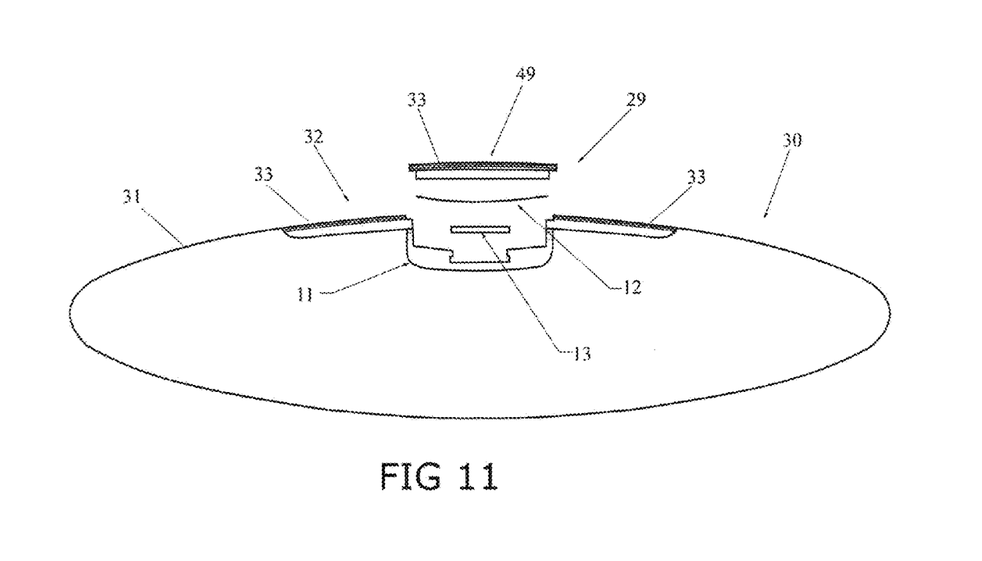
FIG. 11 is a lateral sectional view showing another injection port assembly having the rescaling matrix of the invention.

FIG. 11 is a lateral sectional view of a tissue expander 30 having an injection port structure 29 whereby a resealing silicone matrix cap or cover portion 49 is provided over the injection port structure 29 as well as providing a resealing ring 33 around and extending from the port structure. This configuration eliminates the need for a compression ring around the silicone as shown in FIG. 3 where ring member 15 is utilized to compress the centrally disposed thickened portion 17 of the top portion 14 of the port assembly.

Process of Manufacturing

The process of manufacturing the unitary composite silicone ring and other embodiments of the invention may include the following steps:

1. Two layers of unvulcanized silicone sheeting reinforced with a Dacron polyester mesh or like fiber mesh are applied within a specifically designed mold. These two layers of reinforcement are oppositely oriented and are positioned at the correct depth required to provide the desired self-sealing characteristics.
2. The mold is next filled with an unvulcanized liquid silicone resin (medical grade silicone) to form an injection port and self-sealing silicone composite.
3. The silicone composite within the mold is then cross linked and vulcanized, utilizing the correct amount of heat, time and pressure into an unitary injection port structure (alternative to a two piece design, where the port is separate inside of the tissue expander shell).
4. The injection port is then assembled with the required internal components using room temperature vulcanizing silicone adhesive.
5. The injection port assembly with integrated self-sealing composite ring is then heat vulcanized to the inside surface of the tissue expander using the correct amount of time and pressure.

Subsequent vulcanization, the resultant structure is a unitary, formed, molded structure as shown in the various drawings. The respective individual elements shown and discussed herein are utilized to understand the various structures and embodiments of the invention.

The advantage provided by this invention is a one piece injection port structure having an integrated resealing silicone composite to prevent leakage after an accidental needle puncture near the edge of the injection port. The silicone composite material is designed to reseal after being punctured by a 21-gauge or smaller hypodermic needle, for example. Further, the manufacturing procedure does not require a swelling agent to provide these resealing characteristics. Additionally, the self-sealing characteristics of the resealing composite are not created by encapsulating a silicone gel or other viscous fluid, as described by various pending patents. The fluid path resulting from a needle puncture thru the resealing silicone matrix is compressed closed and effectively sealed due to the elongation restriction created by the correctly and predetermined location and orientation of the reinforced fiber mesh layers. Thus, this invention improves on the prior art by eliminating the need and cost of encapsulating a viscous fluid or gel layer intended to seal a needle path. The two reinforcement layers within the silicone matrix material, positioned at the correct depth and with each layer restricting elongation in at least two directions (oppositely oriented), forces the needle path closed within the silicone rubber substrate as the injection needle is removed and which stops the silicone balloon from leaking.

The present invention further relates to improvements to tissue expander system designs. The improvements provide the patient with the opportunity to be scanned by a Magnetic Resonance Imager (MRI) after having a tissue expander implanted and which may lead to other diagnostic benefits for the patient. The latter not being possible with the use of prior art devices that utilize materials affected by a Magnetic Resonance Imager.

The MR scannable materials used in this invention may be varied to include any material that produces a limited or negligible MRI image distortion or degradation, having a magnetic susceptibility less than about $178 \times 10^{-6}$. Examples of these materials may include: ceramics, graphite, silica, PTFE, PEEK, HDPE, nylon, copper, and/or other materials determined to be non-ferrous, MRI compatible and/or MRI safe.

The term "MR safe" applies to medical devices or materials which are known scientifically to be completely safe within an MRI scanner. Materials that are MR safe include plastics, ceramics and other non-metallic materials. The term "MR conditional" applies to medical devices or materials that have been tested to have a minimal and acceptable reaction to the MRI scanner. These MR conditional products are tested to meet a specific level of magnetic exposure, rated by the Tesla level of the MRI scanner. Normal MRI scanners are 1.5 Tesla but other scanners could create a much greater magnetic force, depending on the scanner being used. The MR conditional products are approved for use based on the Tesla level of the MRI used in the validation testing and safety instruction specifying the Tesla limit are on the product label. Material known to be MR conditional include titanium, stainless steel, or other non-magnetic metals.

Figure 12:
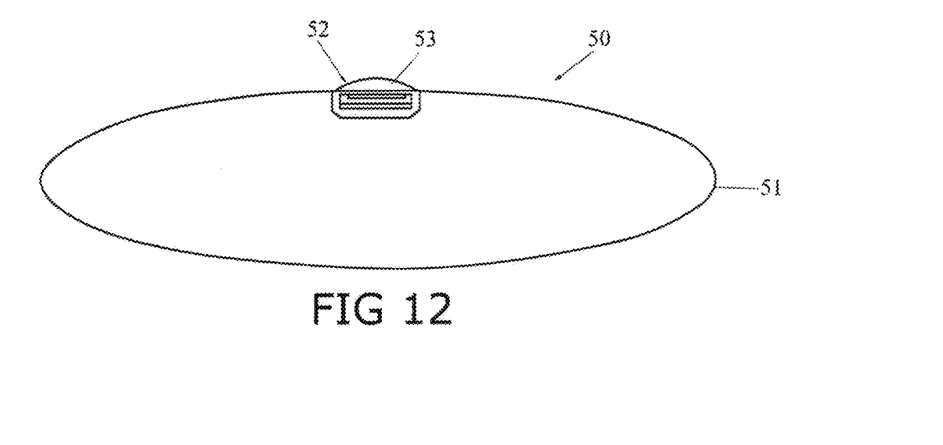
FIG. 12 is a sectional view of an internal MR scannable injection port of the invention and showing the injection port incorporated into a tissue expander, and having a lump for locating the port.

FIG. 12 shows a tissue expander system 50 of the invention utilizing the MR scannable injection port 52. FIG. 12 shows a cross-sectional view of the tissue expander 50 with tissue expander shell 51 using an MR scannable internal injection port 52. Typically, after the tissue expander has been implanted under the patient's skin, the MR scannable internal injection port may be located for filling purposes by the Doctor using the traditional technique of palpitation, which is essentially feeling for a location lump 53 under the skin. A mobile ultrasound device may also be utilized to locate the tissue expander system. Once the port location has been found, the Doctor may then insert a hypodermic needle thru the patient's skin and into the injection port. The Doctor then slowly fills the tissue expander with sterile saline solution, for example.

After multiple injections during various filling schedules, the skin tissue will grow and expand with the device. A typical treatment skin expansion may last multiple months and during this time the patient may need to be scanned by an MRI for diagnostic purposes. If a prior art tissue expander device had been used, for example, this diagnostic treatment would need to be delayed because of the potential harm the MR field imposes on the prior art device. The invention of the MR safe/MR compatible injection port allows the tissue expander and/or mammary prosthesis to be scanned by the MRI, thus allowing for the possibility of earlier detection of other medical issues the patient may need to have treated.

Figure 13:
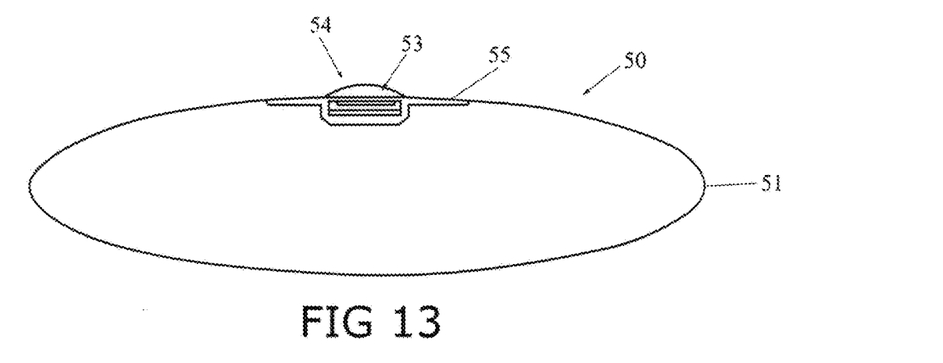
FIG. 13 is a sectional view of an internal MR scannable injection port with an integrated reseal ring and showing the injection port incorporated into a tissue expander, and having a lump for locating the port.

FIG. 13 shows the tissue expander system utilizing the MR scannable internal injection port with an integrated reseal matrix 54. The drawing is another cross sectional drawing of a generic shaped tissue expander using an MR scannable internal injection port with a protective reseal matrix 55 for filling the tissue expander by locating via palpitation the lump 53 adhered to the expander. The integrated resealing composite matrix 55 allows for the tissue expander to self-seal in case of an accidental puncture of a hypodermic filling needle, outside of the intended injection location but still thru the resealing silicone composite material.

Figure 14:
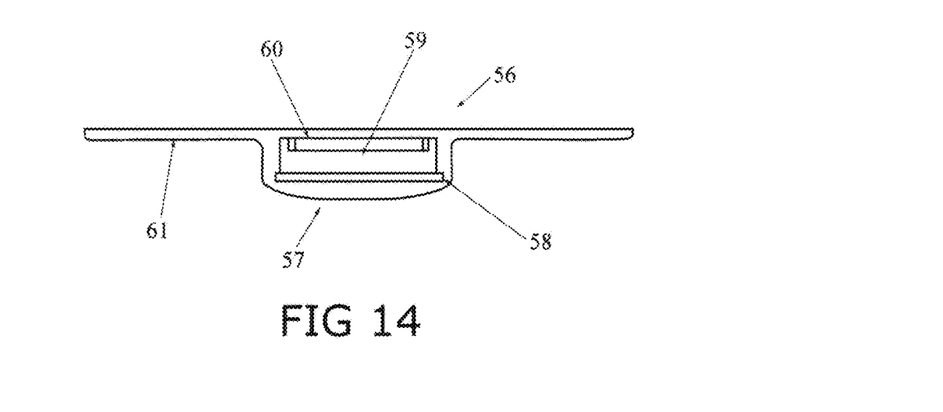
FIG. 14 is a sectional view of the MR scannable injection port with optional integrated protective resealing silicone matrix, to be used inside of a tissue expander and/or mammary prosthesis.

FIG. 14 is a cross-sectional view of an internal MR scannable injection port 56 with the integrated reseal matrix 61. The cross-sectional view of the MR scannable internal injection port 57 is shown having the resealing silicone matrix 61. The MR scannable components and injection fill cavity 59 with the needle stop plate 58 and compression ring 60 is shown. The injection port may also be manufactured without the protective resealing silicone composite matrix material.

Figure 15:
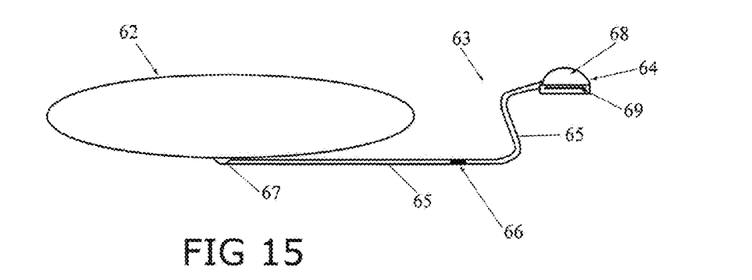
FIG. 15 is a sectional view of a remote MR scannable injection port assembly and showing the MR scannable tubing and tubing connector.

FIG. 15 shows the tissue expander system 62 utilizing the MR scannable remotely located injection port assembly 63 and MR scannable tubing connector 66. The drawing is a sectional view of a tissue expander system using MR scannable materials for a remotely located injection port 63 connected to the tissue expander 62 at connection 67 via silicone tubing 65 and MR scannable tubing connector 66.

Figure 16:
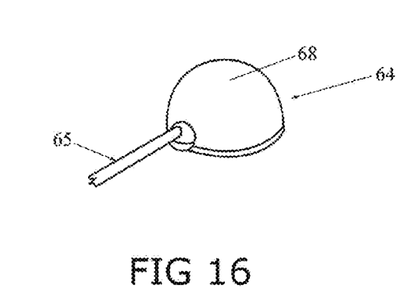
FIG. 16 is a perspective view of the MR scannable injection port assembly of FIG. 15.
Figure 16A:
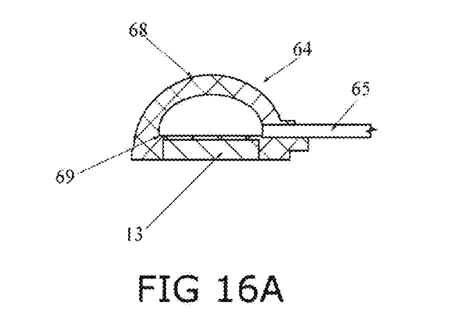
FIG. 16A is a sectional view of the injection port assembly of FIG. 16.

Referring further to FIGS. 15-16A, FIG. 16 shows a perspective view of a remote MR scannable injection port assembly 64 having injection dome 68 and having a needle stop plate 69. The MR scannable tissue expander injection port assembly 64 is shown for remote location and attachment to a tissue expander system 62 with biocompatible tubing 65 utilizing tubing connector 66 and terminating at connection 67 to the tissue expander shell. The needle stop plate 69 used within the remote port 64 is constructed of an MR scannable material that has been sized to a thickness able to withstand the compressive and piercing force created by 21 gauge or smaller hypodermic injection needle. The needle must buckle and/or bend during extreme compressive loading and the needle, thereby, will not penetrate through the MR scannable material. FIG. 16A is a sectional view of the injection port assembly 64 wherein a magnetic member 13 is shown positioned within injection dome 68 and beneath needle stop plate 69. Member 13 may be used for port location purposes. The dome 68 structure may be constructed of the resealable silicone/fiber matrix material discussed herein.

Figure 17:
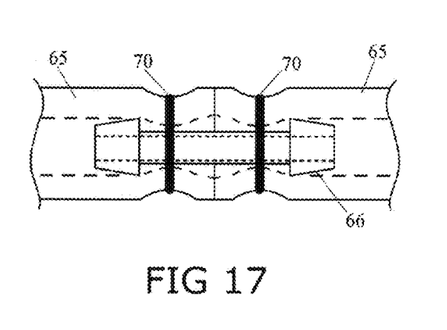
FIG. 17 is a side view of the MR scannable tubing connector utilizing two pieces of silicone tubing and being sutured together.

FIG. 17 is a detailed view of an MR scannable tubing connector 66 sutured together, having two pieces of silicone tubing 65 in series, as shown in FIG. 15. FIG. 17 shows the MR scannable remote port tubing connector 66. The implant grade tubing 65 is typically cut to the desired length by the Doctor and the two tubing ends are sutured 70 to the tubing connector 66. The tubing connector 66 is constructed of an MR scannable material that is able to withstand compressive forces resulting from the suturing process by the Doctor.

The injection area and/or port assemblies shown having MR safe needle stop plates may be formed of, for example, polyether ether ketone (PEEK). PEEK is an organic polymer thermoplastic with excellent mechanical and chemical resistance properties. PEEK is highly resistant to thermal degradation and to attack in organic and aqueous environments. PEEK is an advanced biomaterial for use in medical implants.

Dimensional thickness of the MR scannable materials is critical for the mechanical ability of the injection port assemblies to self seal after being punctured by a needle and to also avoid needle penetration. If the material of choice, for example, is PEEK for the needle stop plate in the MR safe injection port, the material thickness must be thicker than 0.036" to stop and bend a 21 gauge hypodermic needle. A 21 gauge hypodermic needle is typically the largest and the most common needle, 0.032" outside diameter, used for injection of breast and tissue expanders currently used in the industry. The needle stop plate could be increased in thickness without changing effectiveness. Other needle stop plate materials would require a different thickness, depending on the material's mechanical properties.

Figure 18:
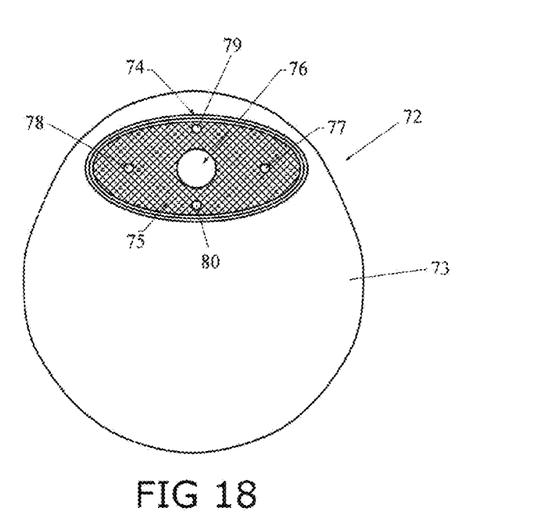
FIG. 18 shows an oval shape MR safe injection port assembly utilizing a resealing matrix as an injection area, and shown located within the upper pole of a breast expander and utilizing multiple location lumps.
Figures 18A, 19:
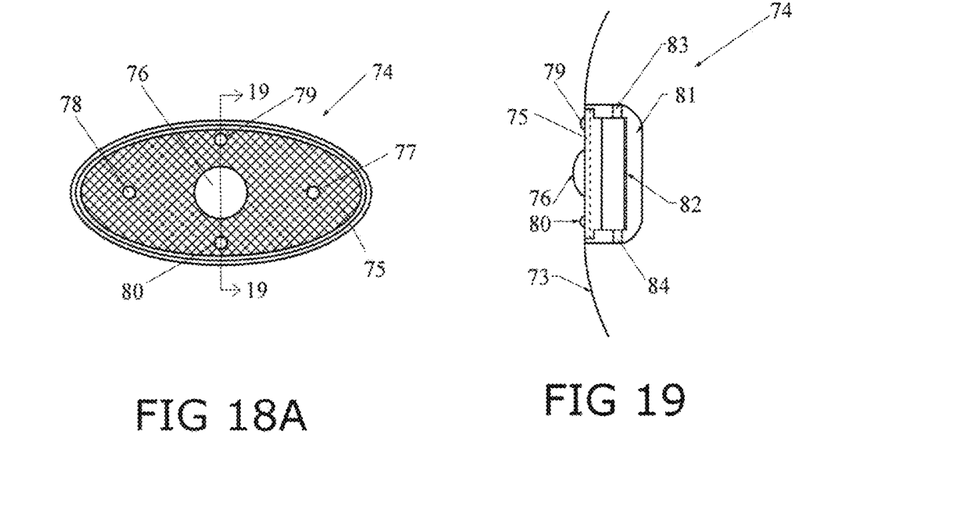
FIG. 18A shows the oval shape/MR safe injection port of FIG. 18.
FIG. 19 is a cross sectional view of the MR safe injection port utilizing the resealing matrix as an injection area and showing the multiple location lumps.

FIGS. 18 and 18A show an MR safe injection port assembly 74 utilizing the resealing matrix as an injection area. Breast expander 72 is shown having a variation of an MR safe injection port assembly 74 in shell 73 that utilizes the reseal matrix 75 to self-seal after needle injections. The injection port structure 74 is shown having the reseal matrix 75 with a center port locating lump 76 and quadrant port locating lumps 77, 78, 79 and 80 spatially positioned from the center lump 76. FIG. 19 is a cross-sectional view of the MR safe injection port of FIG. 18A and which is shown having the reseal matrix structure to self-seal after needle injections. The injection port structure 74 is shown in expander shell 73 having injection port body 81 with the reseal matrix 75 needle stop plate 82 and saline/fluid drain holes 83 and 84. Quadrant port locating lumps 79 and 80 are shown defining the port location with respect to the center port locating lump 76. The palpation or locating lumps may be vulcanized to the tissue expander material in alignment with the port structure. The injection port using the resealing matrix eliminates the need for a compression ring or compression cup. The reseal matrix allows the injection port to be any shape or size, although an oval shape is shown in these drawings. Any desired port parameter shape design may be utilized.

Figure 20:
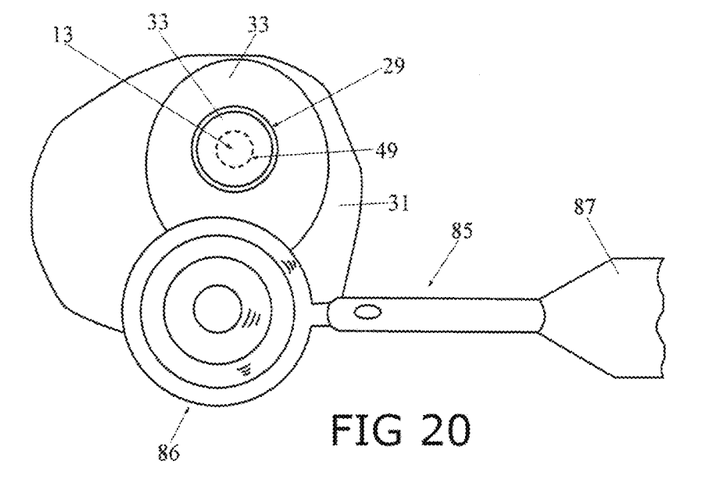
FIG. 20 shows a beat frequency oscillator positioned above the injection port of a tissue expander shell.

FIG. 20 shows a beat frequency oscillator (BFO) 85 having a head portion 86 and a handle portion 87. The BFO 85 may be utilized to detect the position of the resealing port cap portion 49 of the injection port structure 29 of the tissue expander shell 31. The injection port structure 29 may have a stainless steel member 13 therein which is detectable by BFO 85 and thereby providing medical personnel the location of the implanted injection port structure 29 for filling purposes. The use of a stainless steel member 13 provides for an MRI conditional filling port structure whereas the use of a magnetic member would not.

Typically, medical grade silicone is the primary material used to construct tissue expander and mammary prosthesis and which is known to be MR safe. The components required to seal and protect the injection ports and to not allow needle penetration directly through the tissue expander must be made from any material that produce a limited or negligible MRI image distortion or degradation, and/or material that has a magnetic susceptibility less than about $178 \times 10^4$. These MR scannable components include the needle stop plate and any compression ring used in the injection port.

The use of the MR scannable injection port will allow the regular injection of isotonic sterile saline into a tissue expander and/or mammary prosthesis, while not interfering with the patient's ability to be scanned by a Magnetic Resonance Imager.

As many changes are possible to the tissue expander and/or mammary prosthesis injection port embodiments of this invention utilizing the teachings thereof, the descriptions above, and the accompanying drawing should be interpreted in the illustrative and not in the limited sense.

That which is claimed is:

1. A unitary injection assembly for a soft tissue expansion device having an expandable shell formed of a polymeric material comprising:
   a) an injection port body having a bottom portion, a top portion and a peripheral wall;
   b) a resealing ring structure extending outwardly from said top portion of said injection port body, said resealing ring structure formed of a resealing composite silicone matrix material having a top silicone layer, a bottom silicone layer and oppositely oriented polyester fabric sheet layers therebetween to stabilize said resealing ring structure and forming a polymeric fiber matrix material to provide self-sealing properties, said composite silicone matrix material extending outward from said peripheral wall of said injection port body; and
   c) a needle stop member positioned below said top portion of said injection port body of said unitary injection assembly, whereby the oppositely oriented polyester fabric layers provide mechanical forces to stabilize said composite silicone matrix material and to provide the resealing properties.

2. The unitary injection assembly of claim 1, wherein said unitary injection assembly is constructed and arranged to be incorporated into the interior of a polymeric shell of a soft tissue expansion device, wherein said unitary injection assembly is formed of MR scannable materials and wherein said composite resealing ring structure has a shore A durometer reading ranging between 20 and 50.

3. The unitary injection assembly of claim 1, wherein the soft tissue expansion device has a predetermined wall thickness, wherein said top and bottom silicone layers of said resealing composite silicone matrix material each have a thickness greater than the predetermined wall thickness of the soft tissue expansion device and wherein each said polyester fiber sheet layer has a thickness of approximately 0.02 inches.

4. The unitary injection assembly of claim 1, wherein each said polyester fabric sheet layer has a predetermined thickness and wherein said top and bottom silicone layers of said resealing composite silicone matrix material each having a thickness greater than said predetermined polyester fabric sheet layer thickness.

5. The unitary injection assembly of claim 1, wherein said top and bottom silicone layers each have a thickness approximately twice the thickness of said polyester fabric sheet layers and wherein said resealing silicone matrix material ranges in thickness between approximately 0.18 and 0.38 inches.

6. A unitary injection assembly for a soft tissue expansion device having an expandable polymeric shell comprising:
   a) a flexible polymeric structure having an injection area and a resealing matrix material surrounding and extending outwardly from said injection area;
   b) an injection port positioned below said injection area, said injection port having a top portion, a bottom portion and a peripheral wall having fluid egress;
   c) oppositely oriented polyester fabric sheet layers embedded in said flexible polymeric structure and forming a resealing composite matrix material extending outwardly from said injection area; and
   d) a needle stop member positioned below said injection area of said flexible polymeric structure.

7. The unitary injection assembly of claim 6, wherein said flexible polymeric structure is formed of a silicone for vulcanization to the interior of an expandable shell of a soft tissue expansion device formed of a silicone, wherein each said polyester fiber sheet layer has a thickness of approximately 0.02 inches and wherein the fiber mesh of said polyester sheet layers are oppositely oriented between adjacent layers.

8. The unitary injection assembly of claim 6, wherein the soft tissue expansion device has a predetermined wall thickness, wherein said resealing composite matrix material has top and bottom silicone layers and wherein said top and bottom silicone layers have a thickness greater than the predetermined wall thickness of said soft tissue expansion device shell.

9. The unitary injection assembly of claim 8, wherein each said polyester fabric sheet layer has a predetermined thickness, wherein said top and bottom silicone layers of said resealing composite silicone matrix material each has a thickness greater than said predetermined polyester fabric sheet layer thickness.

10. The unitary injection assembly of claim 8, wherein said top and bottom silicone layers each have a thickness approximately twice of said polyester fabric sheet layer thickness.

11. The unitary injection assembly of claim 6, wherein said resealing matrix material has a Shore A durometer reading ranging between 20 and 50.

12. The unitary injection assembly of claim 11, wherein said resealing silicone matrix material ranges in thickness between approximately 0.18 and 0.38 inches.

13. An injection assembly for a soft tissue expansion device having a polymeric shell comprising:
   a) a resealing composite silicone matrix material having oppositely oriented polyester fabric sheets therein to stabilize said composite silicone matrix material, said resealing composite silicone material forming a resealing material without a swelling agent to provide self-sealing properties; and
   c) a needle stop plate positioned below said injection assembly.

14. The injection assembly of claim 13, wherein an injection port body is incorporated in said resealing composite silicone matrix material and incorporated into the interior of a polymeric shell of a soft tissue expansion device, said injection port body having a cover member.

15. The injection assembly of claim 14, wherein said injection assembly and said injection port body are formed of MR scannable materials, said injection assembly further having a port locating device for locating the injection port body subsequent implantation of the soft tissue expansion device.

16. The injection assembly of claim 13, further forming an enclosed port structure having tubing extending therefrom for communication with a polymeric shell of a soft tissue expansion device.

17. The injection assembly of claim 15, wherein said cover member is comprised of said resealing composite silicone matrix material and wherein said injection port locating device is selected from the group of port location devices consisting of a palpation lump, a magnetic source and a metallic source.

18. The injection assembly of claim 17, wherein said injection port locating device comprises at least one palpation lump extending upward from said cover member of said injection port body.

19. The injection assembly of claim 18, wherein said at least one palpation lump includes a center port locating lump and a plurality of locating lumps surrounding and spaced from said center port locating lump.

20. The injection assembly of claim 18, wherein said rescaling composite silicone matrix material has a Shore A durometer reading ranging between 20 and 50.

\* \* \* \* \*